US011179030B2

(12) United States Patent
Shibata et al.

(10) Patent No.: US 11,179,030 B2

(45) Date of Patent: Nov. 23, 2021

(54) ILLUMINATION DEVICE

(71) Applicant: PANASONIC INTELLECTUAL PROPERTY MANAGEMENT CO., LTD., Osaka (JP)

(72) Inventors: Yudai Shibata, Hyogo (JP); Yoshiyuki Takahira, Kyoto (JP); Shintaro Hayashi, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 106 days.

(21) Appl. No.: 16/669,954

(22) Filed: Oct. 31, 2019

(65) Prior Publication Data

US 2020/0138281 A1 May 7, 2020

(30) Foreign Application Priority Data

Nov. 7, 2018 (JP) ............................. JP2018-209579

(51) Int. Cl.

*A61B 1/06* (2006.01)
*F21V 8/00* (2006.01)
*A61B 1/07* (2006.01)

(52) U.S. Cl.

CPC ............ *A61B 1/0653* (2013.01); *A61B 1/063* (2013.01); *A61B 1/07* (2013.01); *G02B 6/0006* (2013.01); *G02B 6/0008* (2013.01)

(58) Field of Classification Search

CPC ......... A61B 1/0653; A61B 1/063; A61B 1/07; G02B 6/0006; G02B 6/0008; G02B 6/001; F21Y 2115/30; F21V 7/0091; F21K 9/61; F21K 9/62; F21K 9/64

See application file for complete search history.

(56) References Cited

U.S. PATENT DOCUMENTS

2007/0024971 A1* 2/2007 Cassarly ............ G02B 27/0994 359/485.03
2009/0040781 A1 2/2009 Ito
2015/0062955 A1* 3/2015 Sorg ........................ F21S 43/16 362/553

FOREIGN PATENT DOCUMENTS

JP 2009-39438 A 2/2009
WO WO-2013140484 A1 * 9/2013 ............. G02B 6/001
WO WO-2013179961 A1 * 12/2013 ......... A61B 1/00126

* cited by examiner

*Primary Examiner* — Erin Kryukova

(74) *Attorney, Agent, or Firm* — Greenblum & Bernstein P.L.C.

(57) ABSTRACT

An illumination device includes a laser light source that emits laser light, a wavelength converter that converts the laser light to converted light of a different wavelength, and a first light guide that mixes the converted light while guiding, and a second light guide that guides the converted light mixed by the first light guide.

9 Claims, 24 Drawing Sheets

ILLUMINATION DEVICE

CROSS REFERENCE TO RELATED APPLICATION

This application claims priority to Japanese Patent Application No. 2018-209579 filed on Nov. 7, 2018, which is incorporated herein by reference in its entirety including the specification, claims, drawings, and abstract.

TECHNICAL FIELD

The present disclosure relates to an illumination device.

BACKGROUND

In the related art, for example, Japanese Unexamined Patent Application Publication No. 2009-39438 discloses an optical fiber illumination device suitable for use with an endoscope. This optical fiber illumination device includes a semiconductor laser, a single fiber, a phosphor unit, and an optical fiber bundle. The semiconductor laser emits excitation light. The single fiber guides the excitation light emitted from the semiconductor laser. The phosphor unit receives the excitation light that has been emitted from the single fiber and emits fluorescence light of a wavelength different from that of the excitation light. The optical fiber bundle guides at least some of waves of the fluorescence light that have been emitted from the phosphor unit.

In the illumination device disclosed in Japanese Unexamined Patent Application Publication No. 2009-39438, the fluorescence light emitted from the phosphor unit is guided by the optical fiber bundle. In this case, because the properties of incident light and output light guided by respective optical fibers forming the optical fiber bundle remain the same, unevenness in hue and luminance, if existing in the fluorescence light from the phosphor unit, remains as it is in the light outputted from the output end.

An object of the present disclosure is to provide an illumination device that can reduce unevenness in hue and luminance of incident light before outputting the light.

SUMMARY

An illumination device according to one aspect of the present disclosure includes a laser light source, a wavelength converter, a first light guide, and a second light guide. The laser source emits laser light. The wavelength converter converts the laser light to converted light of a different wavelength. The first light guide mixes the converted light while guiding. The second light guide guides the converted light mixed by the first light guide.

The illumination device according to one aspect of the present disclosure can reduce unevenness in hue and luminance of incident light before outputting the light.

BRIEF DESCRIPTION OF DRAWINGS

The figures depict one or more implementations in accordance with the present teaching, by way of example only, not by way of limitations. In the figures, like reference numerals refer to the same or similar elements. Embodiments of the present disclosure will be described based on the following figures, wherein.

DETAILED DESCRIPTION

Embodiments according to the present disclosure are described below with reference to the attached drawings. In the description, specifics including shapes, materials, values, and directions are merely examples to facilitate understanding of the present disclosure, and can be changed as required in accordance with applications, purposes, specifications, or any other requirements. When two or more embodiments or variations are described below, any combinations of their features have been expected.

Figure 1:
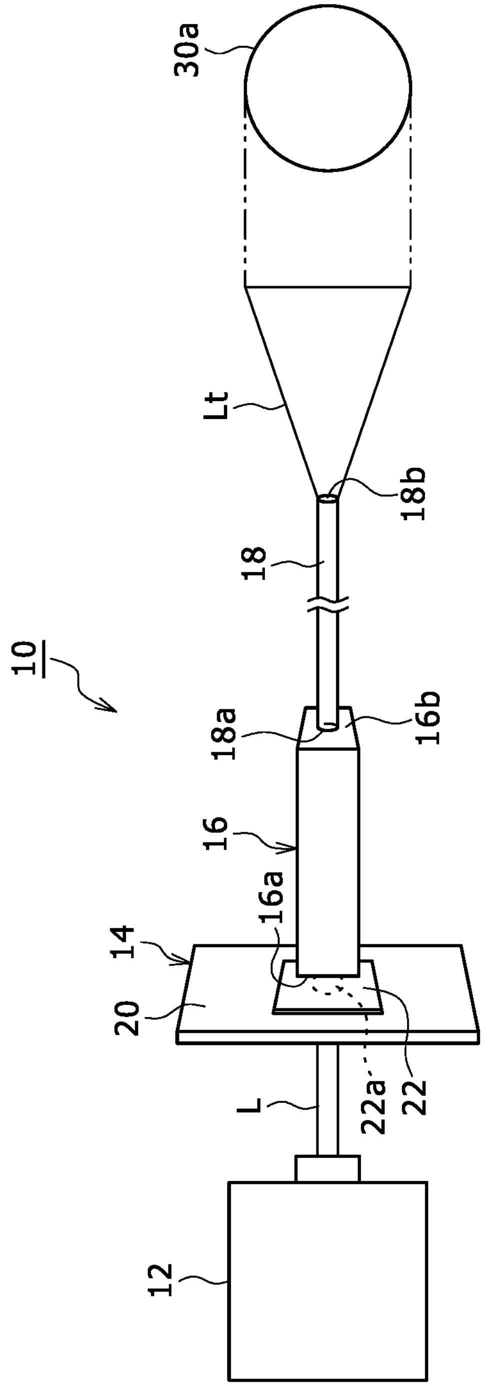
FIG. 1 is a schematic view showing a configuration of an illumination device according to one embodiment of the present disclosure.

FIG. 1 is a schematic view showing a configuration of an illumination device 10 according to one embodiment of the present disclosure. As shown in FIG. 1, the illumination device 10 includes a laser light source 12, a wavelength converter 14, a first light guide 16, and a second light guide 18. The illumination device 10 may be used as illumination for, for example, an endoscope.

The laser light source 12 emits laser light L to the wavelength converter 14. The laser light source 12 includes, for example, a semiconductor laser element. Laser light (excitation light) is emitted by energizing the semiconductor laser element. In the present embodiment, a semiconductor laser element that emits blue laser light of peak wavelength of 430 to 500 nm (in particular, 440 to 465 nm) may be used.

A lens may be disposed between the laser light source 12 and the wavelength converter 14 to collect the laser light L and apply the collected light to the wavelength converter 14. Alternatively, the laser light source 12 may include a condenser lens.

The wavelength converter 14 converts the laser light L to converted light of a different wavelength. The wavelength converter 14 includes a translucent plate 20, and a phosphor 22 formed on a front surface of the plate 20. The laser light L emitted from the laser light source 12 is applied to the phosphor 22 from a rear surface of the plate 20. The area of the phosphor 22 to which the laser light is applied illuminates and emits fluorescence light of a wavelength different from that of the laser light L on the front surface side of the plate 20. In this way, the laser light L is converted by the wavelength converter 14 to converted light of a wavelength different from that of the laser light L.

As the plate 20, for example, a glass plate, a quartz plate, or a sapphire plate may be used. The plate 20 is not limited to a rectangular plate shown in FIG. 1. The plate 20 may have a circular or any other shape.

The phosphor 22 is formed as a thin layer on the front surface of the plate 20, which is the opposite surface to the rear surface of the plate 20 that faces the laser light source 12. Although the phosphor 22 is described to have a rectangular shape as an example in FIG. 1, no limitation is imposed on the shape of the phosphor 22. For example, the phosphor 22 may be a circular or any other shape. In the present embodiment, the phosphor 22 converts a part of the blue laser light L to, for example, yellow light of a peak wavelength of 540 to 570 nm. Thus, the blue light which has not been absorbed by the phosphor 22 and the yellow light whose wavelength has been converted by the phosphor 22 are diffused and mixed in the phosphor 22. As a result, white light is emitted from the wavelength converter 14. The phosphor 22 may be covered by a protective layer made of a transparent resin material to prevent the phosphor 22 from being damaged or peeled off from the plate 20.

In the phosphor 22 of the wavelength converter 14 in the present embodiment, the converted white light is emitted from a surface other than the incident surface that the laser light L enters. Specifically, the laser light L that has passed through the translucent plate 20 is applied to the rear surface of the phosphor 22, which faces the plate 20, and the white light is emitted from a front surface of the phosphor 22, which is the opposite surface from the plate 20. Thus, the wavelength converter 14 of the present embodiment is a translucent wavelength converting device.

As shown in FIG. 1, in the phosphor 22 of the wavelength converter 14, the white light is emitted from a light emission area 22*a* that has an oval shape of a diameter larger than that of the laser light L. An input end 16*a* of the first light guide 16 is disposed to face the light emission area 22*a*. The hue or luminance of the color emitted from the light emission area 22*a* may not be entirely uniform. For example, at the center of the light emission area 22*a*, the blue light may be relatively strong, whereas around the peripheral edge of the light emission area 22*a*, light in which the color after conversion is relatively strong at a luminance lower than the center color may be emitted.

Figure 2:
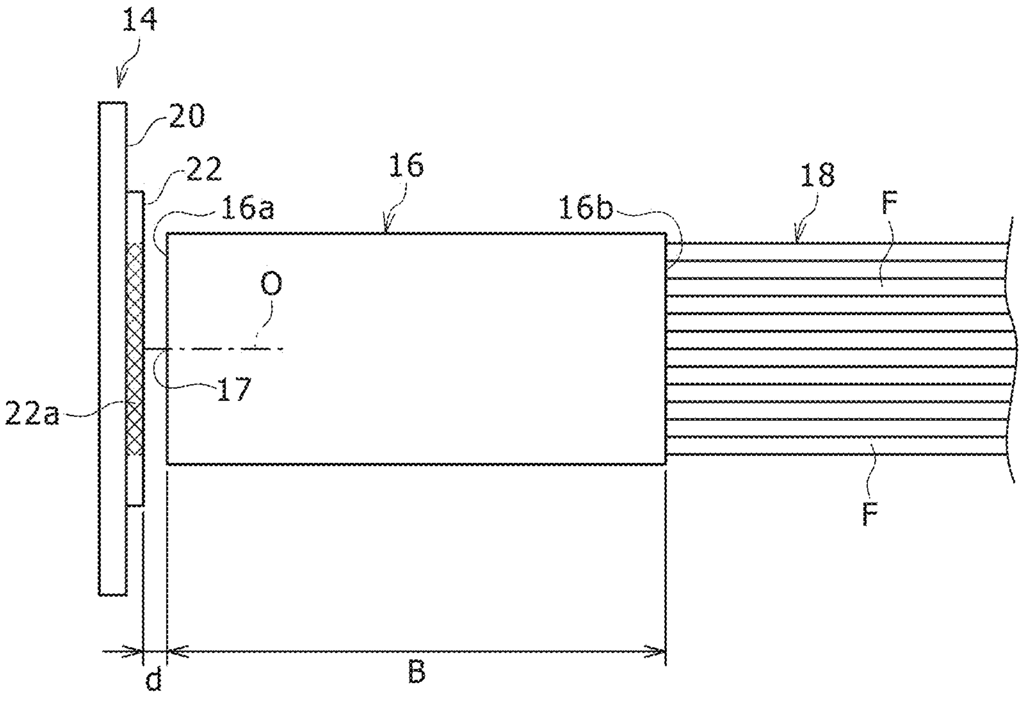
FIG. 2 is a side view showing a wavelength converter, a first light guide, and a second light guide in the illumination device of FIG. 1.

FIG. 2 is a side view showing the wavelength converter 14, the first light guide 16, and the second light guide 18 in the illumination device 10 shown in FIG. 1. In FIG. 2, the light emission area 22*a* of the phosphor 22 is cross hatched.

As shown in FIGS. 1 and 2, the first light guide 16 includes the input end 16*a* and an output end 16*b*, and has uniform cross sections between the input end 16*a* and the output end 16*h*. The first light guide 16 mixes the light emitted from the phosphor 22 of the wavelength converter 14, while guiding the light.

Figure 3A:
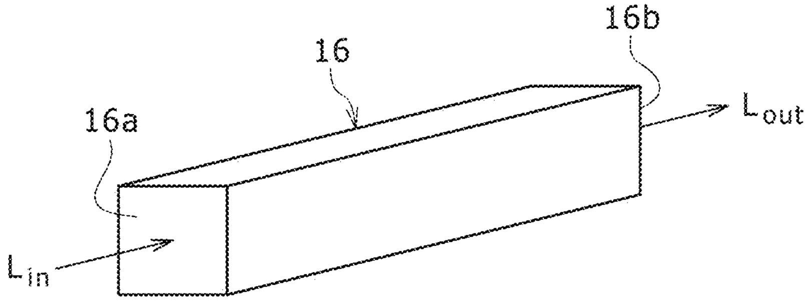
FIG. 3A is a perspective diagram showing a first light guide formed from a glass rod.
Figure 3B:
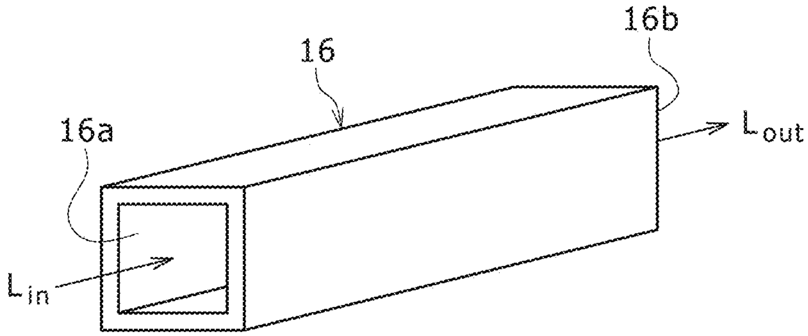
FIG. 3B is a perspective diagram showing another first light guide formed from a mirror rod.

The first light guide 16 may be formed from a glass rod or a mirror rod. FIG. 3A is a perspective view of the first light guide 16 formed from a glass rod. FIG. 3B is a perspective view of the first light guide 16 formed from a mirror rod. As shown in FIG. 3A, when the first light guide 16 is formed from the glass rod, the solid internal portion that has a rectangular cross section serves as a light-guiding portion. In this case, the first light guide 16 has a rectangular solid shape. FIG. 3A shows an embodiment which the cross section of the first light guide 16 between the input end 16*a* and the output end 16*b* is rectangular. It has been confirmed that the uniformity indicating how evenly the incident light is mixed becomes favorable when the cross section of the first light guide 16 is rectangular. This is described in more detail further below.

In the first light guide 16, light $L_{in}$ that enters from the input end 16*a* propagates through the solid light-guiding portion inside the first light guide 16, and light $L_{out}$ is emitted from the output end 16*b*. When the cross section of the first light guide 16 is rectangular, the light is reflected inwards at an outer surface of the first light guide 16 while propagating. In this way, the light is uniformly mixed and the light $L_{out}$ is emitted from the output end 16*b*. As a result, because the first light guide 16 reduces unevenness in hue and luminance in the incident light $L_{in}$, the light $L_{out}$ achieving evenness in hue and luminance can be emitted.

As shown in FIG. 3B, when the first light guide 16 is formed from a mirror rod, the internal space having a rectangular cross section serves as the light-guiding portion. In this case, the first light guide 16 has a rectangular hollow shape. The internal surface of the mirror rod is made from a mirrored material. The light $L_{in}$ that has entered from the input end 16*a* is reflected at an inner surface of the first light guide 16 while propagating, and the light $L_{out}$ is emitted from the output end 16*b*. Similarly to the case of a solid, because unevenness in hue and luminance of the light $L_{in}$ is reduced, the light $L_{out}$ achieving evenness in hue and luminance can be emitted.

As shown in FIG. 2, the first light guide 16 may be arranged relative to the wavelength converter 14 such that an optical axis O of the light emission area 22*a* is aligned to the center of the input end 16*a*, and the optical axis O of the light emission area 22*a* is perpendicular to the input end 16*a*. By arranging the first light guide 16 in this way, the white light emitted from the phosphor 22 of the wavelength converter 14 can be efficiently directed into the first light guide 16.

Regarding the first light guide 16, the aspect ratio B/A may be 2 or higher, where A represents a square root of the cross-sectional area of the light-guiding portion, and B represents the length of the first light guide 16 along the optical axis O. With this arrangement, unevenness in hue and luminance can be sufficiently reduced because a length along the optical axis sufficient to mix the incident light can be ensured. In the first light guide 16 of a tapered type shown in FIG. 5, the aspect ratio B/A can be calculated by assuming the area of the input end 16*a* as the cross-sectional area of the light-guiding portion.

Further, the first light guide 16 may be fixed to achieve a uniform distance d between the wavelength converter 14 and the input end 16*a* which the light from the wavelength converter 14 enters. In this way, the amount of light that enters the first light guide 16 from the wavelength converter 14 can be maintained constant. Such a configuration can be achieved, for example, by fixing the wavelength converter 14 to a chassis (not shown) and attaching the first light guide 16 to the chassis with brackets (not shown). The distance d may be equal to or shorter than ⅓ of the diameter of the input end 16*a*. Specifically, the constant distance indicates that the distance between the wavelength converter 14 and the input end 16*a* is maintained equal to or shorter than ⅓ of the diameter of the input end 16*a*. The distance d may be zero (the wavelength converter 14 is in contact with the input end 16*a*). In this case, if the first light guide 16 is formed from a glass rod, the input end 16*a* may be damaged, lowering transmission efficiency. Because of easy handling of the input end 16*a*, the first light guide 16 may be formed from a mirror rod.

As shown in FIGS. 1 and 2, the second light guide 18 includes an input end 18*a* and an output end 18*b*. The input end 18*a* is disposed to face the output end 16*b* of the first light guide 16 either in contact with or in close proximity to it. The input end 18*a* of the second light guide 18 is connected to the output end 16*b* via a connector element (not shown). The second light guide 18 may be formed from an optical fiber bundle including multiple optical fibers F. Because the second light guide 18 is flexible, when the illumination device 10 is applied to an endoscope, the second light guide 18 can be freely bent in a direction sufficient for progress or observation in an intricate organ. The outer surface of the second light guide 18 is covered by a flexible protection tube (not shown). The number of the optical fibers F of the second light guide 18 may be determined as required in accordance with the diameter and specifications of the endoscope, or other requirements.

The light emitted from the output end 16*b* of the first light guide 16 enters into the input end 18*a* of the second light guide 18, and is guided by the respective optical fibers F of the second light guide 18, and then outputted from the output end 18*b*. The light Lt outputted from the second light guide 18 expands in a fan shape and a target is irradiated with the light. FIG. 1 shows a circular irradiation area 30*a* when a planer surface is irradiated with the light Lt. The circular irradiation area 30*a* is brightly illuminated by high-luminance light with reduced unevenness in hue and luminance, generated by the laser light. Thus, when the illumination device 10 is applied to an endoscope, organs can be more clearly observed, assisting in improving accuracy in diagnosis.

Depending on the type of the applied endoscope, the second light guide 18 may be branched in the middle to have two or more output ends 18*b*, or the output end 18*b* may have a curved surface. Because, with the illumination device 10, the light guided through respective optical fibers of the second light guide 18 has evenness in hue and luminance, emitted light can be uniform, regardless of the number, shape, or arrangement of the output ends. When the illumination device 10 is applied to an endoscope, the accuracy of diagnosis can be expected to be improved regardless of the structure of the endoscope.

Figure 4:
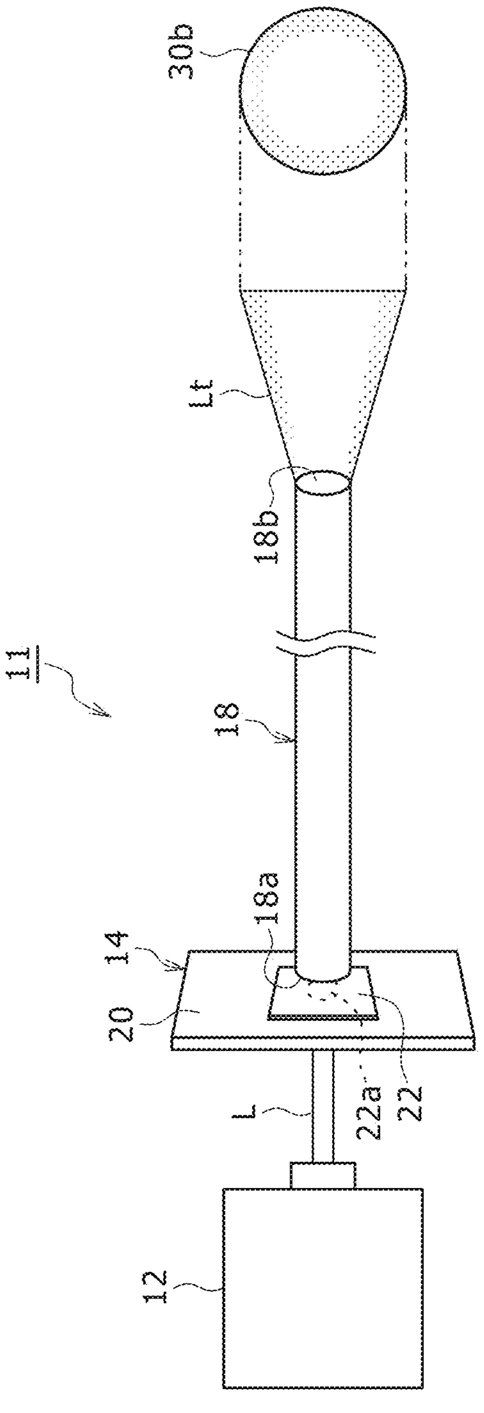
FIG. 4 is a schematic view showing a configuration of an illumination device without the first light guide.

FIG. 4 is a schematic diagram showing a configuration of an illumination device 11 that does not include the first light guide 16. In FIG. 4, shaded areas represent the areas Where unevenness in hue and luminance occurs in the light outputted from the second light guide 18, and an irradiation area.

In FIG. 4, because the illumination device 11 does not include the first light guide 16, the input end 18*a* of the second light guide 18 is disposed to face the light emission area 22*a* of the phosphor 22 of the wavelength converter 14. As described above, in the light emission area 22*a*, the hue or luminance of the light is uneven between a center area and a peripheral area. For example, in the center area of the light emission area 22*a*, light of strong blue may be emitted, whereas in the peripheral area of the light emission area 22*a*, light of strong after-conversion color with a luminance lower than in the center area may be emitted. When such incident light having unevenness in hue and luminance is guided through the second light guide 18 including multiple optical fibers, the light Lt outputted from the output end 18*b* also includes unevenness in hue and luminance as in the incident light. Accordingly, unevenness also occurs between the center area and the peripheral area in an irradiation area 30*b* irradiated with the outputted light Lt. As described above, when the output end 18*b* is formed to have a curved shape, the unevenness in hue and luminance becomes stronger than with the output end 18*b* of a flat shape.

As described above, because of the unevenness in hue and luminance of the light guided through the respective optical fibers F of the second light guide 18, when two or more output ends 18*b* are included, the hue and luminance of the light outputted from the respective output ends become uneven between the two or more irradiation areas 30*b*.

As described above, the illumination device 10 according to embodiments of the present disclosure includes the laser light source 12, the wavelength converter 14, the first light guide 16, and the second light guide 18. The laser light source 12 emits laser light L. The wavelength converter 14 converts the laser light L to converted light of a different wavelength. The first light guide 16 mixes the converted light and the laser light while guiding. The first light guide 16 can efficiently reduce unevenness in hue and luminance of the incident light. As a result, when the illumination device 10 is applied to an endoscope, organs can be more clearly observed, assisting in improvement in accuracy of diagnosis.

In the illumination device 10 according to embodiments of the present disclosure, the light-emission surface of the wavelength converter 14 from which the converted light is emitted is a surface other than the surface that the laser light L enters. Specifically, the wavelength converter 14 includes the translucent plate 20 and the phosphor 22 that is formed on a front surface of the plate 20. The laser light L is applied to the phosphor 22 from the rear surface of the plate 20, and the converted light is emitted on the front surface side of the plate 20 from the phosphor 22. Thus, the wavelength converter 14 is a translucent wavelength conversion device.

In the illumination device 10 according to embodiments of the present disclosure, the first light guide 16 may be formed from a glass rod or a mirror rod.

Figure 5:
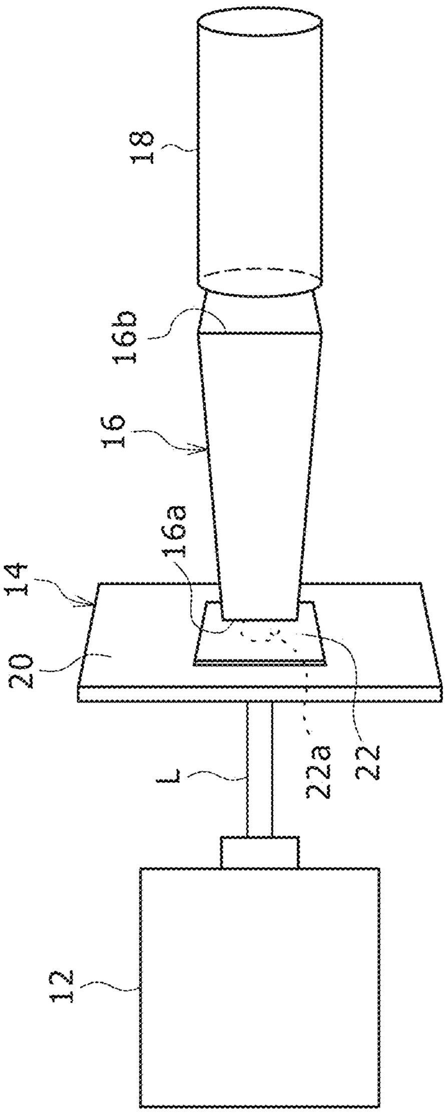
FIG. 5 is a schematic view showing an embodiment of the first light guide of a tapered type.

Further, as shown in FIG. 5, the first light guide 16 in the illumination device 10 according to an embodiment of the present disclosure may have a tapered shape such that the cross-sectional area of the output end 16*b* is larger than the cross-sectional area of the input end 16*a*. The first light guide 16 of a tapered shape can achieve advantages. For example, it becomes easier to optically couple the first light guide 16 to the second light guide 18 of a larger diameter than the first light guide 16. Further, because the light emission angle from the output end 16*b* can be set narrower, it becomes easier to couple the first light guide 16 to fibers of a low numerical aperture (NA).

The first light guide 16 is disposed between the wavelength converter 14 and the second light guide 18. According to this configuration, unevenness in hue and luminance of the incident light from the wavelength converter 14 can be reduced or eliminated by the first light guide 16 before passing the light to the second light guide 18.

The second light guide 18 may be an optical fiber bundle.

In the first light guide 16, the cross section of the light-guiding portion to which the laser light L is guided may have a rectangular shape. The aspect ratio between the square root A of the cross-sectional area of the light-guiding portion and the length B of the first light guide 16 along the optical axis may be 2 or higher. In this way, because a sufficient length along the optical axis required to mix the incident light can be obtained, unevenness in hue and luminance of the incident light can be effectively reduced.

The output end 16*b* of the first light guide 16 may be larger than the input end 18*a* of the second light guide 18. In this way, the light with the reduced unevenness in hue and luminance can be applied to the entire surface of the input end 18*a* of the second light guide 18.

The first light guide 16 may be fixed to achieve a uniform distance d between the wavelength converter 14 and the input end 16*a* which the converted light from the wavelength converter 14 enters. In this way, the amount of light that enters the first light guide 16 from the wavelength converter 14 can be maintained constant.

Figure 6A:
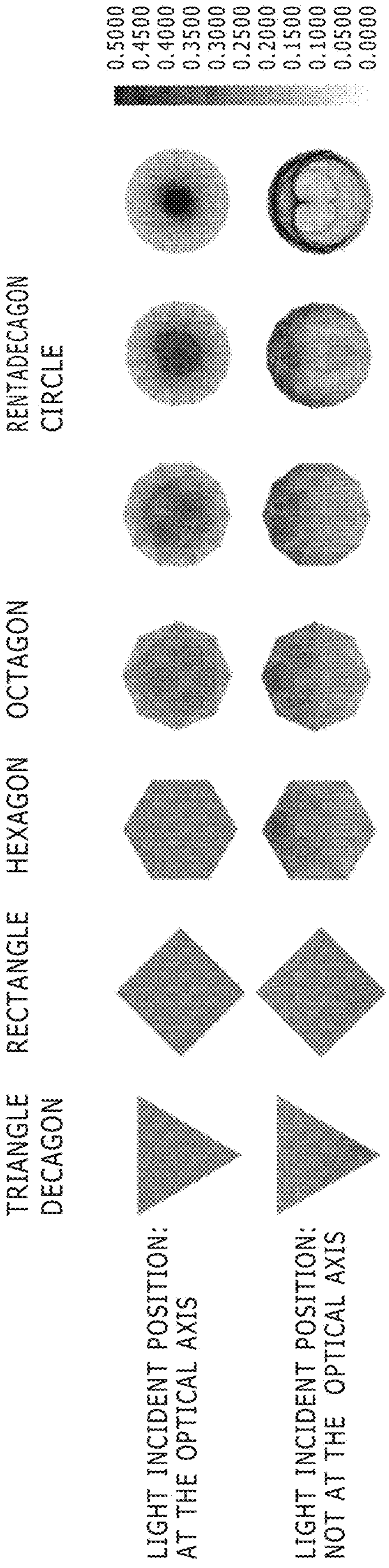
FIG. 6A is a series of grayscale images showing simulation results of relationships between different shapes of a light-guiding portion of the first light guide and uniformity.
Figure 6B:
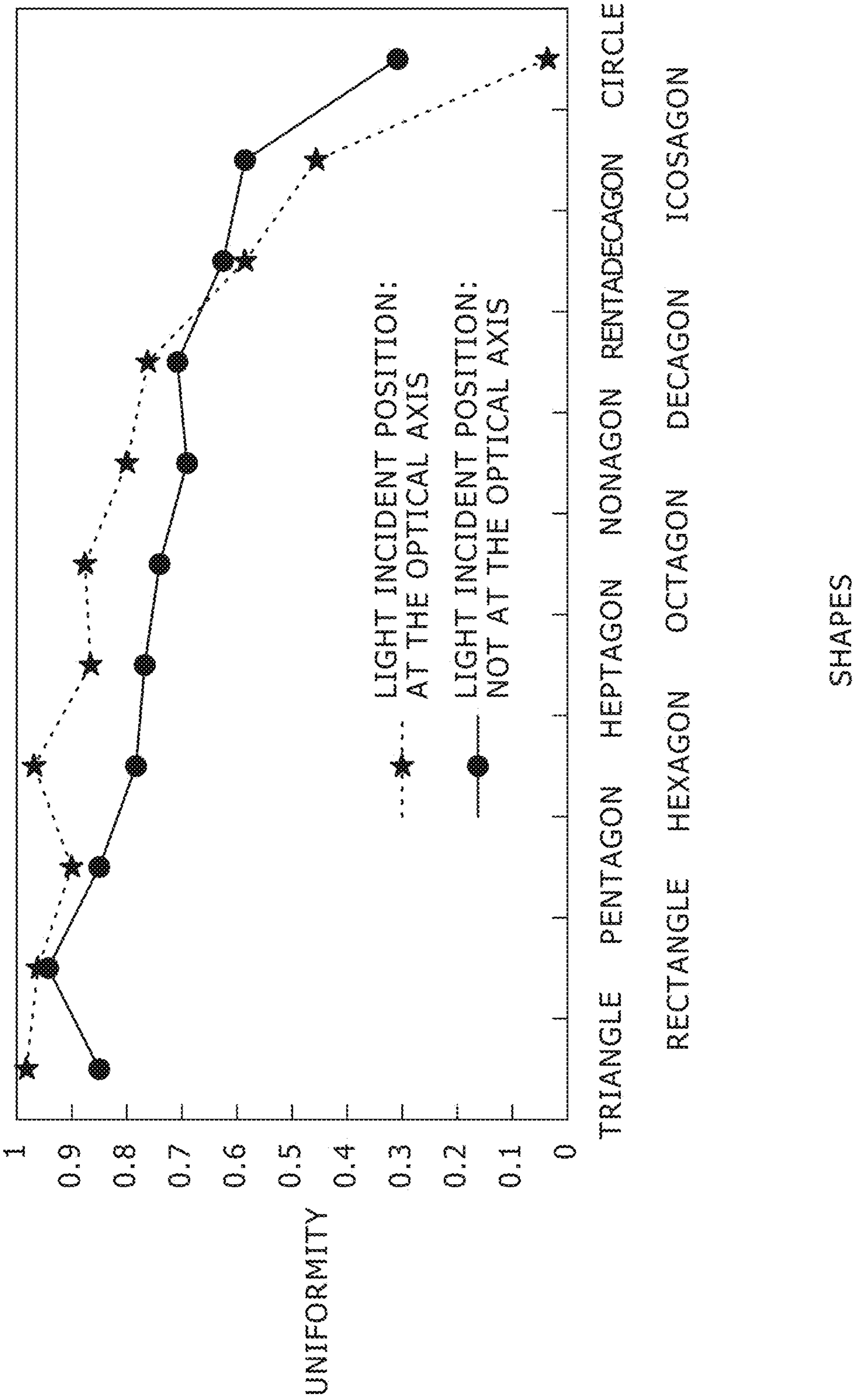
FIG. 6B is a graph showing simulation results of relationships between different shapes of the light-guiding portion of the first light guide, and uniformity.

FIG. 6A is a series of grayscale images showing simulation results of relationships between different shapes of the light-guiding portion of the first light guide 16 and uniformity. FIG. 6B is a graph showing simulation results of relationships between different shapes of the light-guiding portion of the first light guide 16 and uniformity. As shown in FIG. 6A, in these simulations, the uniformity (in other words, degree of light mixing) was analyzed with various cross-sectional shapes of the light-guiding portion of the first light guide 16, namely, triangle, rectangle, hexagon, octagon, decagon, pentadecagon, and circle. In the grayscale images in FIG. 6A, the image of each cross-sectional shape including larger high-contrast portions indicates that unevenness in hue and luminance is significant. For the first light guide 16 including the light-guiding portion of each cross-sectional shape, the aspect ratio N/A was maintained constant at 2.

For each cross sectional shape of the light-guiding portion, analysis was performed for two cases, one with the light incident position at an optical axis, and the other with the light incident position not at the optical axis. As shown in FIG. 2, "at an optical axis" indicates that the position of the optical axis O of the light emission area 22*a* is aligned to the center 17 of the input end 16*a* of the first light guide 16. In contrast, "not at the optical axis" indicates that the optical axis O of the light emission area 22*a* is deviated from the center 17 of the input end 16*a* of the first light guide 16. Unevenness in hue and luminance tended to more likely occur with the light incident position not at the optical axis than at the optical axis.

In the graph in FIG. 6B, the horizontal axis represents the respective cross-sectional shapes of the light-guiding portion of the first light guide 16, whereas the vertical axis represents the uniformity. For the uniformity, with "1" at the maximum value, a smaller number indicates a higher unevenness in hue and luminance of the emitted light $L_{out}$ (refer to FIG. 3).

As shown in FIG. 6A, it was found that the unevenness in hue and luminance was effectively reduced when the cross-sectional shape of the light-guiding portion of the first light guide 16 was a polygon with 10 or less vertexes. As shown in FIG. 6B, among the polygons with 10 or less vertexes, a rectangle was found to be the most suitable shape because the uniformity with the light incident position not at the optical axis achieved the highest value.

Figure 7A:
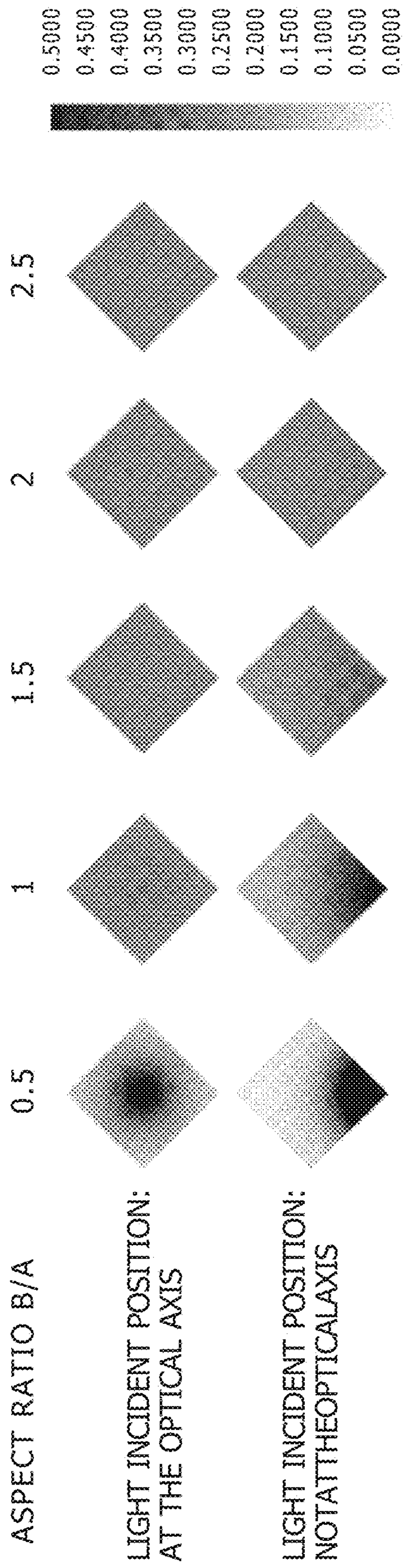
FIG. 7A is a series of gray scale images showing simulation results of uniformity of light obtained by varying aspect ratios with the first light guide including a rectangular light-guiding portion.
Figure 7B:
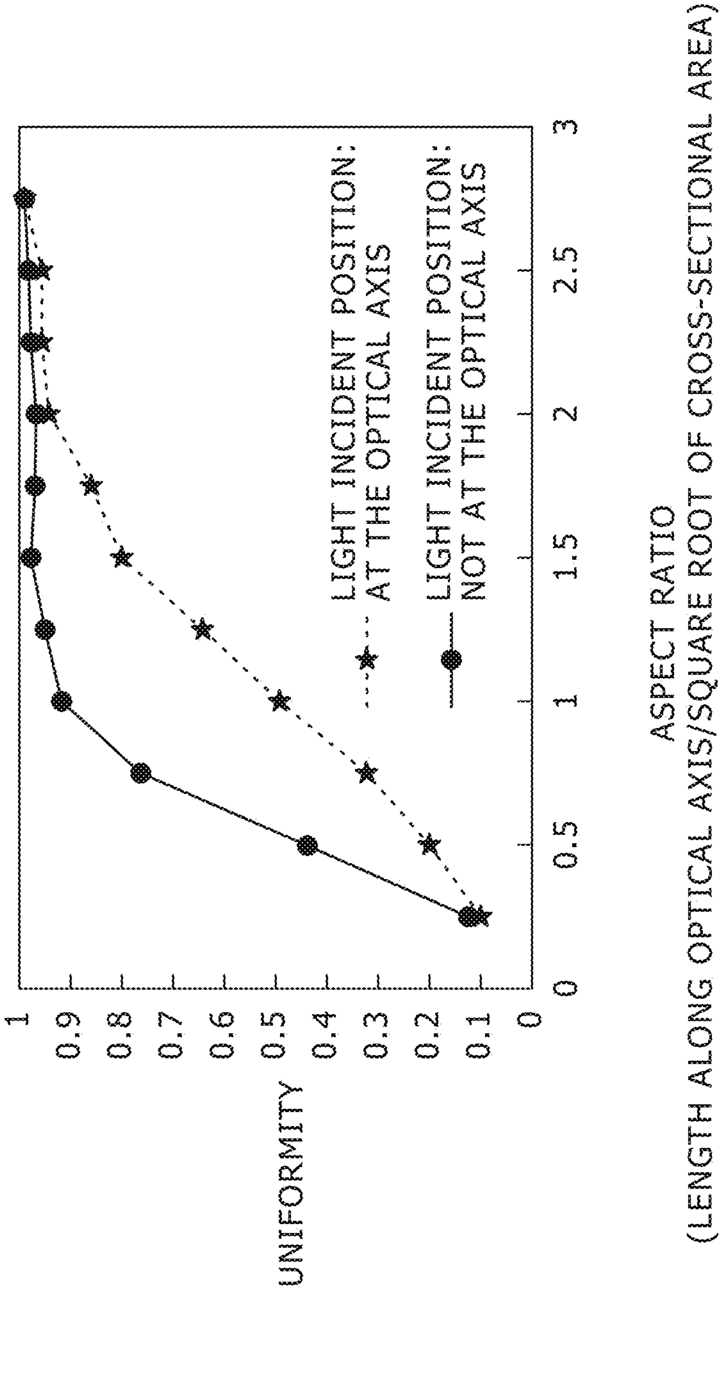
FIG. 7B is a graph showing simulation results of uniformity of light obtained by varying aspect ratios with the first light guide including the rectangular light-guiding portion.

FIG. 7A is a series of grayscale images showing simulation results of light uniformity obtained by changing the aspect ratio with the rectangular light-guiding portion of the first light guide 16. FIG. 7B is a graph showing simulation results of the light uniformity obtained by changing the aspect ratio with the rectangular light-guiding portion. As shown in FIG. 7A, in the simulation, the uniformity was analyzed for two cases, one with the light incident position at the optical axis, and the other with the light incident position not at the optical axis, while changing the aspect ratio B/A to 0.5, 1, 1.5, 2, and 2.5. In the graph in FIG. 7B, the horizontal axis represents the aspect ratio B/A, whereas the vertical axis represents the uniformity. The position at the optical axis, the position not at the optical axis, and the uniformity are the same as those in FIGS. 6A and 6B. In the gray scale images in FIG. 7A, each of the cross-sectional images including larger high-contrast portions indicates that unevenness in hue and luminance is significant.

As shown in FIGS. 7A and 7B, the uniformity was almost 1 for both of the positions (at and not at the optical axis) when the aspect ratio was 2 or higher. Accordingly, it has been confirmed that, in the first light guide 16, a favorable uniformity can be obtained when the aspect ratio is 2 or higher.

Although the embodiments according to the present disclosure describe a wavelength converter of blue laser light to yellow light, no limitation is imposed on the configuration. When multiple phosphors are used as the phosphors 22, in configurations of the related art, unevenness in hue and luminance at the output end 18*b* is significant depending on the temperature properties and the luminance-saturation properties of the respective phosphors. In contrast, in the configurations of the embodiments according to the present disclosure, unevenness in hue and luminance can be reduced. Favorable results were obtained also by using a combination of blue-violet laser of 365 to 430 nm and multiple RGB phosphors.

Figure 8:
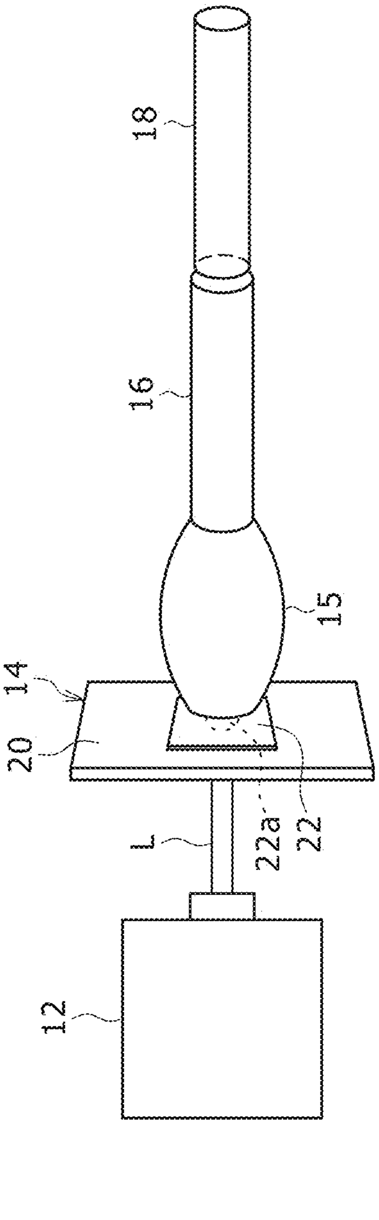
FIG. 8 is a schematic view showing a configuration example in which an oval mirror is disposed between the wavelength converter and the first light guide.

An optical element may be disposed between the wavelength converter 14 and the first light guide 16. For example, as shown in FIG. 8, an oval mirror 15 may be disposed between the wavelength converter 14 and the first light guide 16. In this case, the light emission area 22*a* may be disposed in the vicinity of a first focal point of the oval mirror 15, whereas the input end 16*a* may be disposed in the vicinity of a second focal point of the oval mirror 15. In such an arrangement, the fluorescent light can be efficiently coupled to the first light guide 16.

Figure 9:
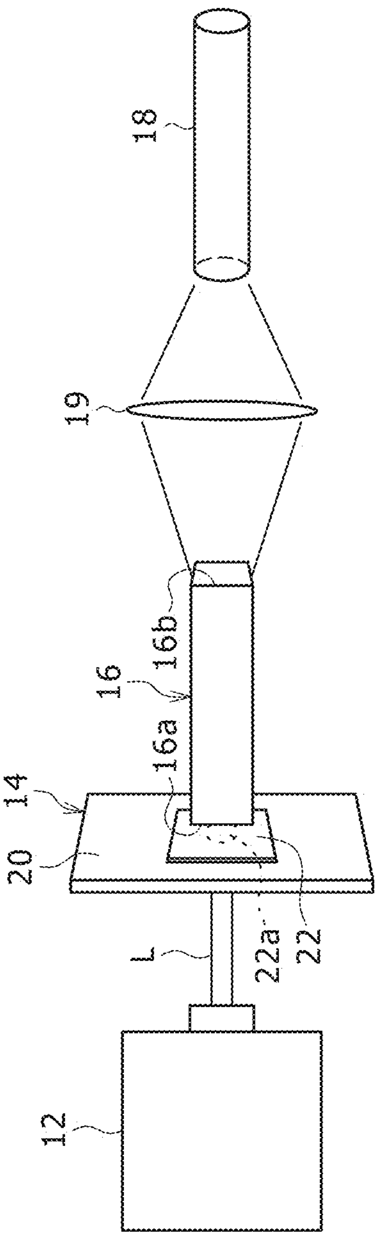
FIG. 9 is a schematic view showing another configuration example in which a lens is disposed between the first light guide and the second light guide.

As shown in FIG. 9, an optical element may be disposed between the first light guide 16 and the second light guide 18. FIG. 9 shows an embodiment in which a lens 19 is disposed between the first light guide 16 and the second light guide 18. This configuration enables light from the first light guide 16 to be coupled to the second light guide 18 that is thinner than the first light guide 16 without unevenness in hue and luminance. In this case, in order to improve a coupling efficiency, the lens 19 having a low chromatic aberration and the second light guide 18 having an NA larger than that of the first light guide 16 may be selected.

Figure 10:
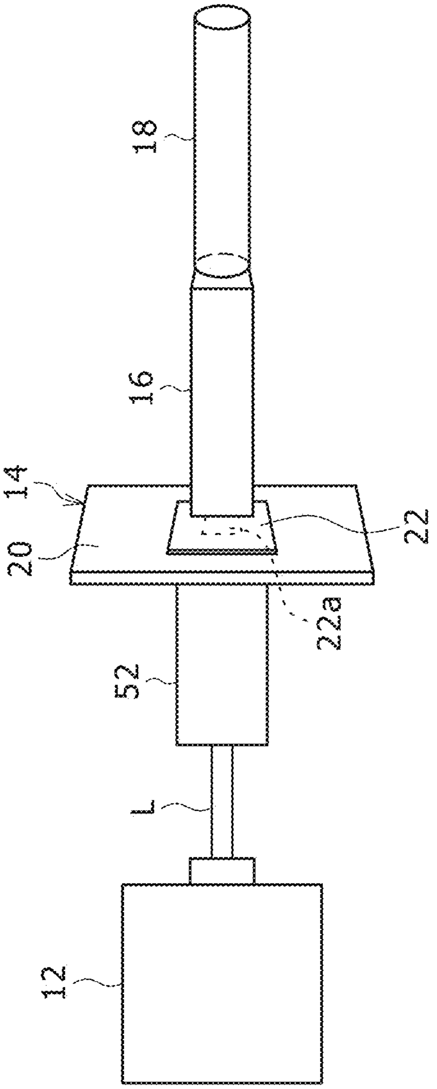
FIG. 10 is a schematic view showing yet another configuration example in which a third light guide is disposed between the laser light source and the wavelength converter.

As shown in FIG. 10, a third light guide 52 that has the same function as the first light guide 16 may be disposed between the laser light source 12 and the wavelength converter 14. In such a configuration, the laser light L can be applied to the phosphor 22 without unevenness. In this way, unevenness in luminance in the light emission area 22*a* can be reduced, making it easier to achieve an advantage of the present embodiment. Further, because unevenness in luminance can be reduced in the light emission area 22*a*, laser light can be converted to fluorescence light without the luminance or thermal saturation, improving fluorescence light conversion efficiency.

Figure 11:
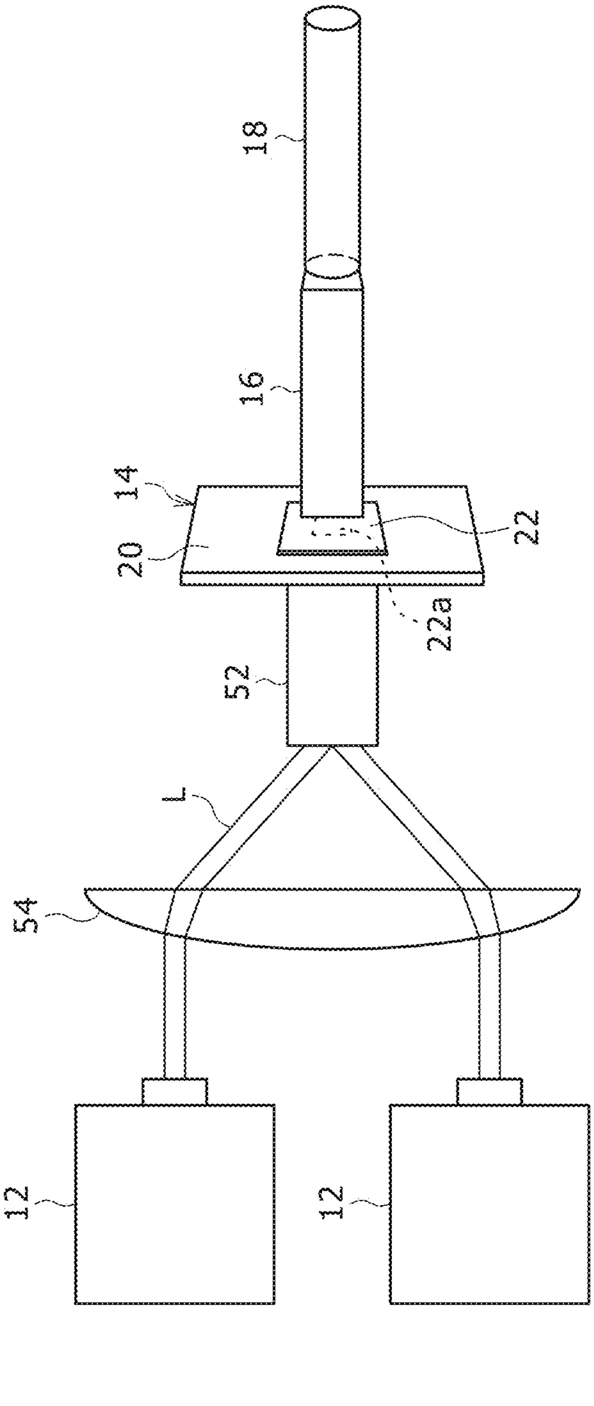
FIG. 11 is a schematic view showing yet another configuration example in which laser light from two or more laser light sources is applied to the third light guide.

By using this configuration, the laser light L from two or more laser light sources 12 (although FIG. 11 shows a case with two laser light sources 12, three or more laser light sources 12 may be used) may be applied to and guided in the third light guide 52, enabling excitation of light from the wavelength converter 14 to a high uniformity. No limitation is imposed on the size and length of the third light guide 52. For example, the light input portion of the third light guide 52 may have an opening of 1×1 mm, and the length of the third light guide 52 may be 8 mm.

In the present embodiment, the peak wavelength of the laser light sources 12 is 455 nm. As the third light guide 52, a mirror rod including dielectric multilayers coated on the internal surface is used. The mirror rod is designed in view of optical efficiency such that when the light in a band of 445 to 465 nm wavelength corresponding to the wavelength of the laser light sources 12 is applied to the third light guide 52, 99% or more light can be emitted. As the first light guide 16, a dielectric mirror rod including dielectric multilayers coated on the internal surface is used. The mirror rod is designed in view of optical efficiency such that when the light in a band of 420 to 680 nm wavelength corresponding to the wavelength and the fluorescence wavelength of the laser light sources 12 is applied to the first light guide 16, 95% or more light can be emitted. However, no limitation is imposed on the configuration. Reduction of unevenness in luminance, which is an object of the present disclosure, can be improved without any issues even when a mirror rod or a glass rod having a low optical efficiency is used. When an optical efficiency is also important in a combination of, for example, blue-violet laser and multiple RGB phosphors, a light guide suitable for the wavelength may be used.

Generally, in order to control a luminance distribution of the light emission area 22*a* when using two or more laser light sources 12, it is necessary to accurately align the laser light L. In contrast, in the configuration according to the present embodiment, because the light is only required to enter the third light guide 52, the alignment is simple, enabling use of a simple and cost effective mechanism to perform the alignment control.

Figure 12:
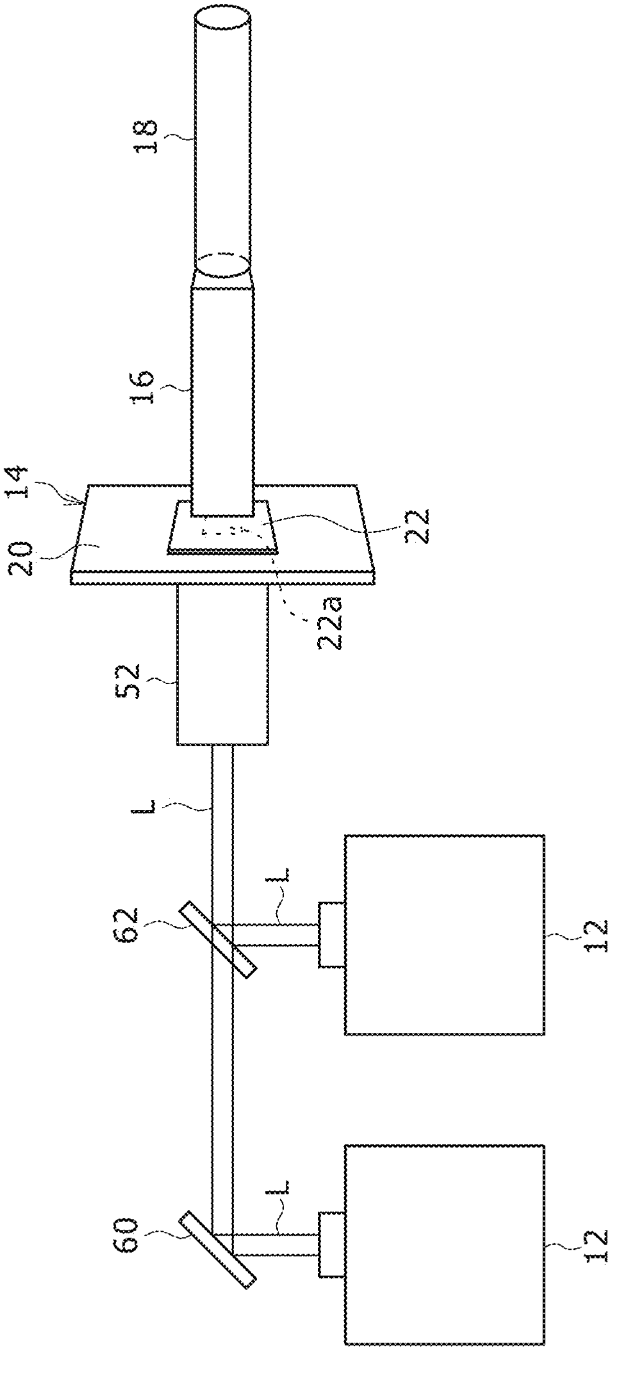
FIG. 12 is a schematic view showing yet another configuration example in which laser light from two or more laser light sources is applied to the third light guide via a mirror and a beam splitter.
Figure 13:
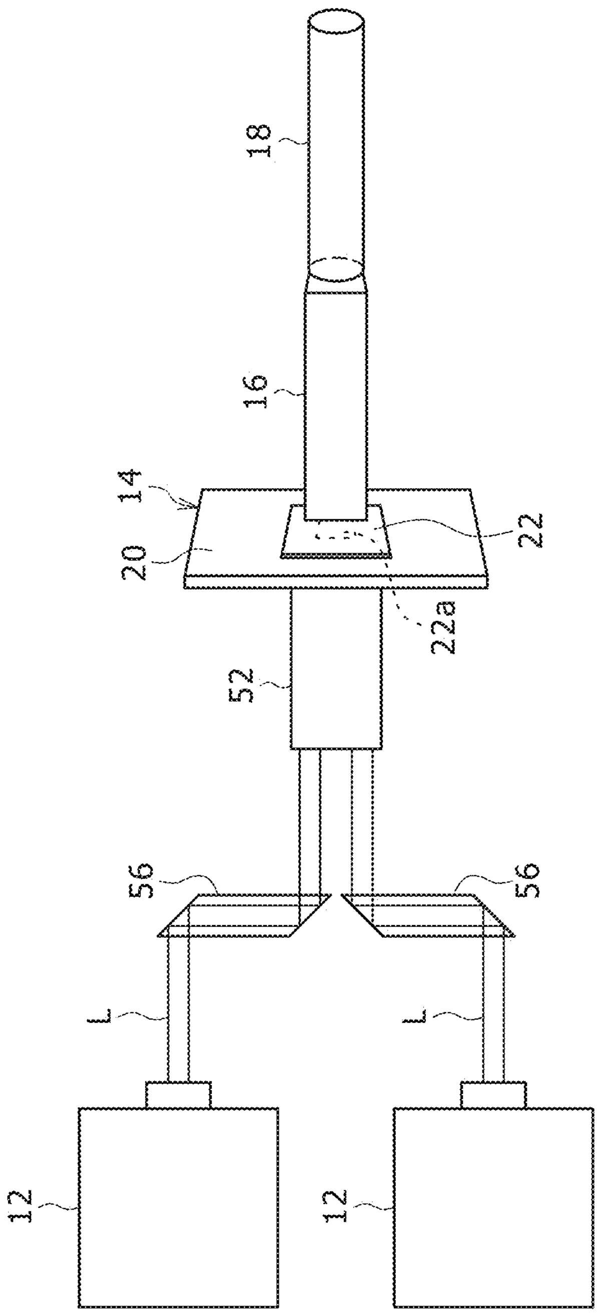
FIG. 13 is a schematic view showing yet another configuration example in which laser light from two or more laser light sources is applied to the third light guide via prisms.

Although a lens is used as the optical element in FIG. 11, a mirror may be used instead. As a method for collecting light into the third light guide 52, prisms 56 may be used as shown in FIG. 13. Alternatively, as shown in FIG. 12, polarization synthesis or wavelength synthesis using a mirror 60 and a beam splitter 62, or a combination thereof may be used.

Figure 14A:
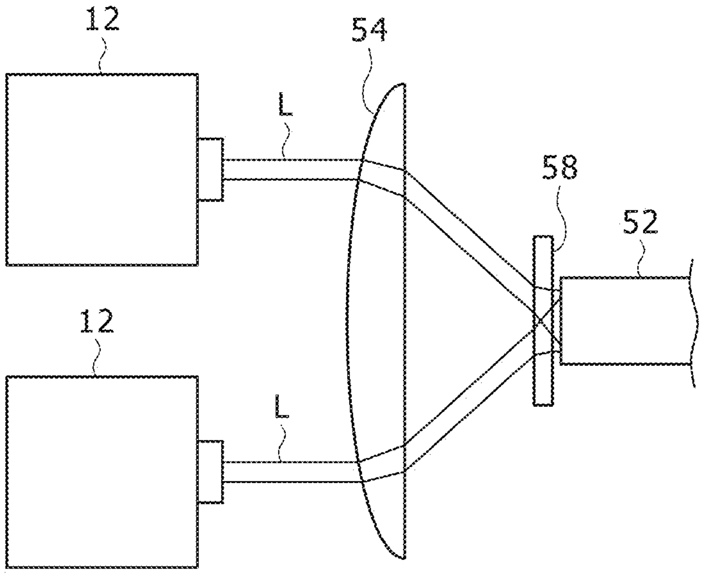
FIG. 14A is a schematic view showing yet another configuration example in which a diffusion plate is disposed upstream of the third light guide in FIG. 11.
Figure 14B:
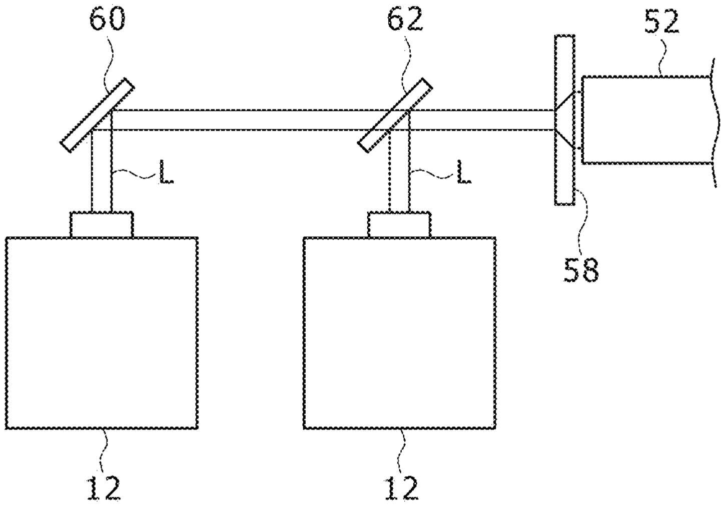
FIG. 14B is a schematic view showing yet another configuration example in which a diffusion plate is disposed upstream of the third light guide in FIG. 12.
Figure 14C:
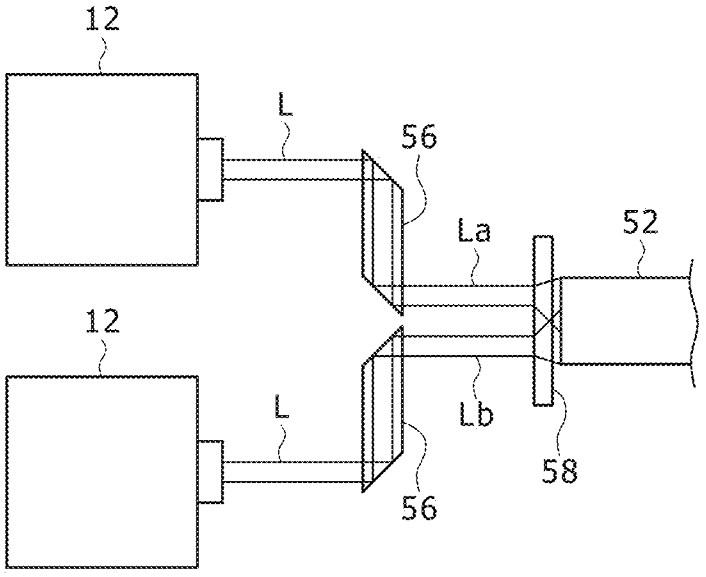
FIG. 14C is a schematic view showing yet another configuration example in which a diffusion plate is disposed upstream of the third light guide in FIG. 13.

FIGS. 14A, 14B, and 14C show embodiments in which a diffusion plate 58 is disposed upstream f the third light guide 52. FIGS. 14A, 14B, and 14C correspond to the respective configurations shown in FIGS. 11, 12, and 13. In the present embodiment, by disposing the diffusion plate 58 upstream of the third light guide 52, the uniformity of light at the output end of the third light guide 52 can be increased even with the third light guide 52 of a shorter length than a case without the diffusion plate 58. By setting the distance between the diffusion plate 58 and the third light guide 52 to be shorter than the square root of the cross-sectional area of the third light guide 52, the light coupling efficiency can be improved.

Figure 15A:
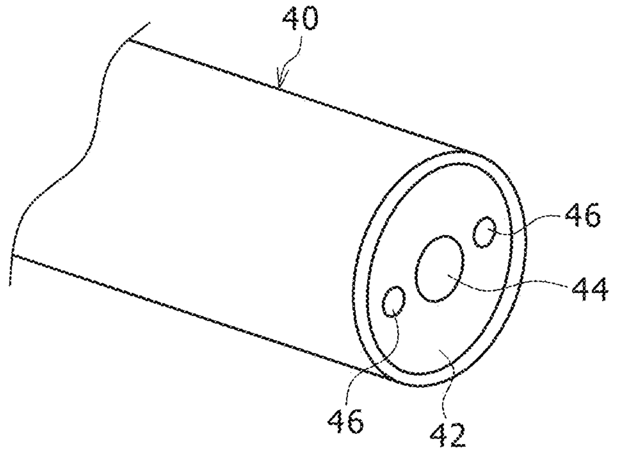
FIG. 15A is an enlarged view of a distal end portion of an endoscope.
Figure 15B:
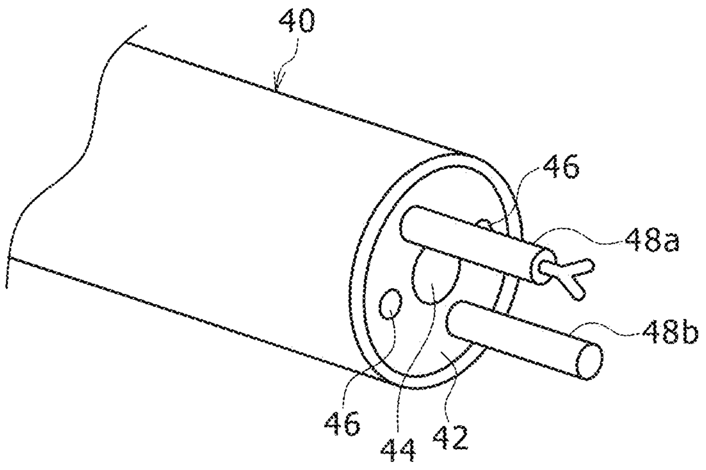
FIG. 15B is an enlarged view of a distal end portion of another endoscope.

FIGS. 15A and 15B are enlarged views of distal ends of the endoscopes 40. The endoscope 40 may be a flexible endoscope suitable for observation of a stomach, a lung, or a colon, or a rigid endoscope suitable for observation of a liver, an elbow, or a knee.

At the distal end 42 of the endoscope 40 shown in FIG. 15A, a camera 44 is disposed at the center, whereas two illumination portions 46 are disposed on both sides of the camera in a diameter direction. When the above described illumination device 10 is applied to the endoscope 40 shown in FIG. 15A, two optical fibers F may form the second light guide 18, and the output ends of the respective optical fibers F may be used as the illumination portions 46.

At the distal end 42 of the endoscope 40 shown in FIG. 15B, in addition to the camera 44 and the two illumination portions 46 shown in FIG. 15A, two surgical tools 48*a*, 48*b* are disposed. In this case, the surgical tools 48*a*, 48*b* may be operated by a control section (not shown) disposed at a proximal end of the endoscope 40.

In the endoscopes 40 shown in FIGS. 15A and 15B, no limitation is imposed on the number of the illumination portions 46. Three or more illumination portions 46 may be used.

Figure 16:
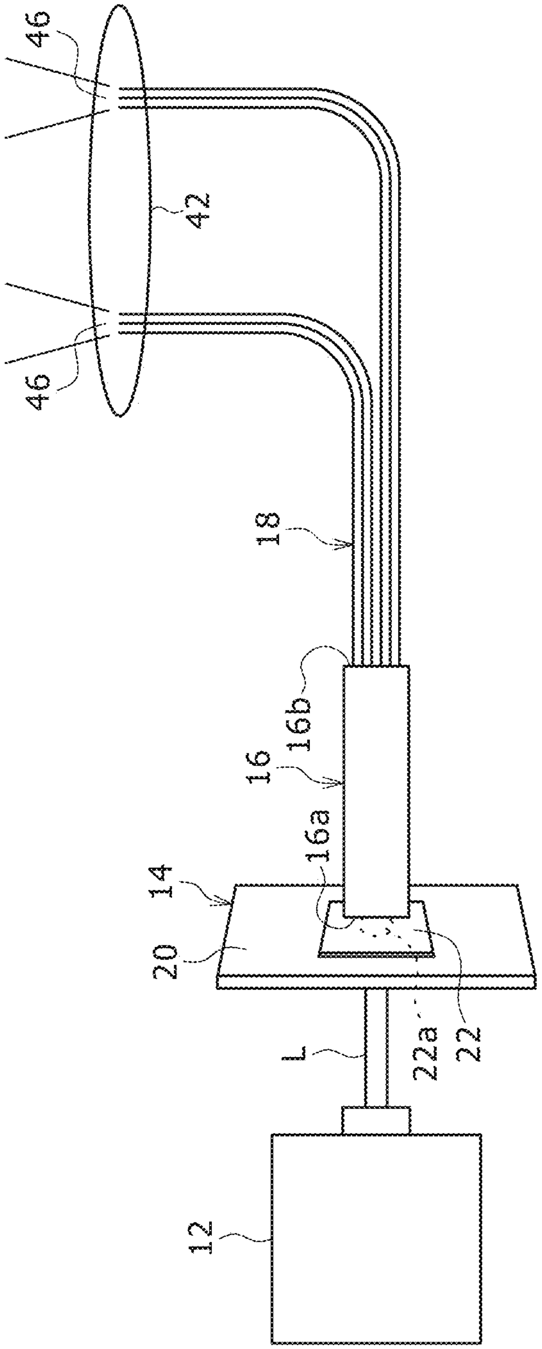
FIG. 16 is a schematic view showing yet another configuration example in which illumination portions at the distal end of the endoscope are formed from optical fiber bundles.

Each of the illumination portions 46 may or may not be a single optical fiber. As shown in FIG. 16, each of the illumination portions 46 may be an optical fiber bundle.

Figure 17:
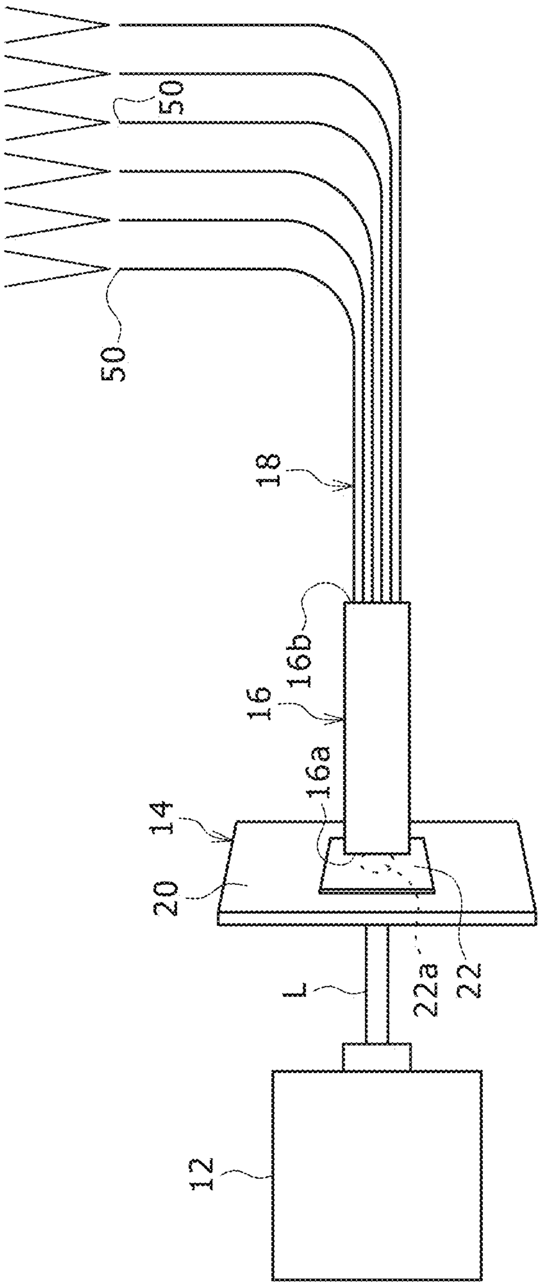
FIG. 17 is a schematic view showing yet another configuration example of the illumination device according to an embodiment of the present disclosure, suitable for general lighting tools.

The illumination device according to embodiments of the present disclosure is not limited to being used for an endoscope, but is applicable to general lights. FIG. 17 shows an embodiment in which the second light guide 18 is branched into six lighting tools 50. When multiple lighting tools 50 are installed, slight difference in chromaticity or luminance flux between the lighting tools 50 may be noticeable, causing complaints. In contrast, by using the configurations of embodiments according to the present disclosure, it becomes possible to reduce difference in chromaticity or luminance flux between the lighting tools 50.

Figure 18:
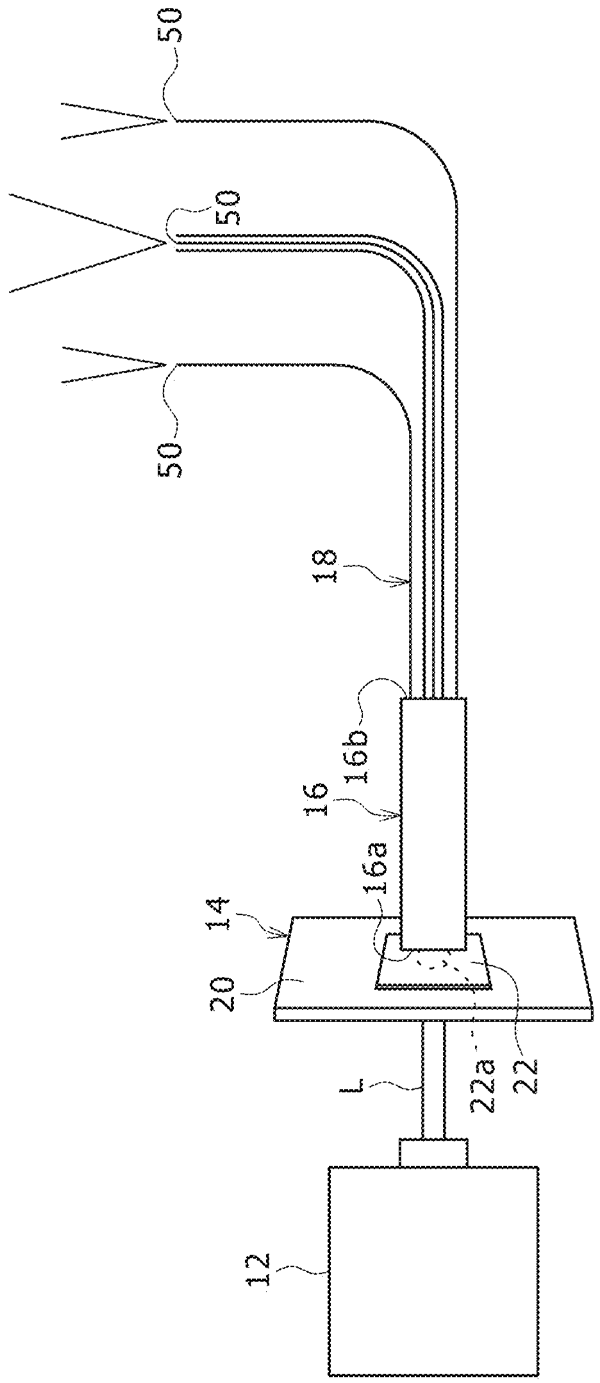
FIG. 18 is a schematic view showing yet another configuration example in which the number of optical fibers connected to each of the general lighting tools differs from each other.

The number of the lighting tools 50 is not limited to six. As shown in FIG. 18, the number can be determined as required. Further, the number of optical fibers for each lighting tool 50 can be varied, and the luminance of each lighting tool 50 can be varied by changing the number of optical fiber bundles.

The applications of the illumination device according to embodiments of the present disclosure are not limited to the above embodiments or their variations. Various modifications and improvements within the matters described in the attached claims of the present application are possible.

The invention claimed is:

1. An illumination device comprising:

a laser light source emitting laser light;

a wavelength converter converting the laser light to converted light of a different wavelength;

a first light guide mixing the converted light while guiding; and a second light guide guiding the converted light mixed by the first light guide, wherein an output end of the first light guide is larger than an input end of the second light guide.

2. The illumination device according to claim 1, wherein in the wavelength converter, a light-emission surface from which the converted light is emitted is a surface other than an incident surface that the laser light enters.

3. The illumination device according to claim 2, wherein the wavelength converter comprises a translucent plate and a phosphor formed on a front surface of the plate, and the laser light is applied to the phosphor from a rear surface of the plate, and the converted light is emitted on a front surface side of the plate from the phosphor.

4. The illumination device according to claim 1, wherein the first light guide is either a glass rod or a mirror rod.

5. The illumination device according to claim 1, wherein the first light guide is disposed between the wavelength converter and the second light guide.

6. The illumination device according to claim 1, wherein the second light guide is an optical fiber bundle.

7. The illumination device according to claim 1, wherein a cross-sectional shape of a light-guiding portion of the first light guide is a polygon with 10 or less vertexes.

8. The illumination device according to claim 1, wherein a cross-sectional shape of a light guiding portion of the first light guide for guiding the laser light is a rectangle, and an aspect ratio between a square root of a cross-sectional area of the light-guiding portion and a length of the first light guide along an optical axis is 2 or higher.

9. The light illumination device according to claim 1, wherein the first light guide is fixed to maintain a constant distance between the wavelength converter and an input end to which the converted light from the wavelength converter is applied.

* * * * *